United States Patent [19]
Huffman et al.

[11] Patent Number: 4,749,782
[45] Date of Patent: Jun. 7, 1988

[54] VASOPRESSIN COMPOUNDS

[75] Inventors: William F. Huffman, Malvern; Michael L. Moore, Media; Nelson C. Yim, Ambler, all of Pa.

[73] Assignee: Smithkline Beckman Corporation, Philadelphia, Pa.

[21] Appl. No.: 27,769

[22] Filed: Mar. 19, 1987

Related U.S. Application Data

[63] Continuation-in-part of Ser. No. 782,671, Oct. 2, 1985, abandoned.

[30] Foreign Application Priority Data

Oct. 1, 1986 [EP] European Pat. Off. ........ 86307580.0

[51] Int. Cl.$^4$ .............................................. A61K 37/02
[52] U.S. Cl. ..................................... 530/328; 530/329
[58] Field of Search ................... 530/328, 329; 514/16

[56] References Cited

PUBLICATIONS

Manning et al., "Design of Potent and Selective Antagonists of the Vasopressor Responses to Arginine-Vasopressin", *J. Med. Chem.*, 1982, 25, 406–414.

Manning et al., "Synthesis and Some Pharmacological Properties of 18 Potent O-Alkyltyrosine-Substituted Antagonists of the Vasopressor Responses to Arginine-Vasopressin", *J. Med. Chem.*, 1985, 28, 1485–1491.

*Primary Examiner*—Delbert R. Phillips
*Assistant Examiner*—Nathan M. Nutter
*Attorney, Agent, or Firm*—Janice E. Williams; Stuart R. Suter; Alan D. Lourie

[57] ABSTRACT

Certain vasopressin-like compounds whose structures have a $\beta,\beta$-diethyl-$\beta$-mercaptopropionic acid at position 1 have unexpectedly potent V$_2$-antagonist activity. A species of the group is [1-$\beta,\beta$-diethyl-$\beta$-mercaptopropionic acid)-2-(O-ethyl-D-tyrosine)-4-valine-8-arginine-9-desglycine]vasopressin.

16 Claims, No Drawings

VASOPRESSIN COMPOUNDS

This application is a continuation-in-part of application Ser. No. 782,671 filed Oct. 2, 1985, which is now abandoned.

This invention relates to [1-($\beta$,$\beta$-diethyl-$\beta$-mercaptopropionic acid)-2-(O-ethyl-D-tyrosine)-4-valine-8-arginine]vasopressin compounds which have unexpected aquaretic activity. Pharmaceutical compositions and methods for inducing water diuresis (aquaretic activity) in patients in need thereof are also part of this invention.

BACKGROUND OF THE INVENTION

M. Manning et al., J. Med. Chem. 25 406 (1982), discloses certain compounds related in structure to those of the present invention. Note that Manning's series of compounds involve structures which have L-tyrosine at position 2. The compounds, particularly the 1-$\beta$-,$\beta$-diethyl-$\beta$-mercaptopropionic acid congeners, are also described as potent VSP antagonists at $V_1$-receptor sites which results in anti-vasopressor activity. The compounds were also determined to have weak agonist or anti-diuretic activity at $V_2$-receptor sites. Finally, Manning concludes that predictability in this field was uncertain, even within closely related structural pairs of compounds.

The Manning publication, along with earlier patent applications filed by our assignee such as Ser. No. 673,828 now U.S. Pat. No. 4,599,324, 673,829 now U.S. Pat. No. 4,604,378 and 747,646 now U.S. Pat. No. 4,640,120, indicate that substitution of an acyclic propionic acid unit at position 1 of VSP-like structures increase antagonism at $V_1$ (pressor) receptors and decrease or reverse antagonism at $V_2$ (antidiuretic) receptors. Contrary to these teachings, we have now found that VSP-like compounds which have a Tyr(Et) unit at position 2 and a Mpr(Et) unit at position 1 of their structures have very potent $V_2$-antagonistic properties. Therefore, they have useful water diuretic properties. The compounds of this invention are the first potent $V_2$-antagonists whose structures do not have a spiroalkyl-containing propionic acid at position 1 in the VSP art to the best of our knowledge.

In the description herein and in the claims, the nomenclature common in the art of peptide and, more specifically, vasopressin chemistry is used. When no configuration is noted, the amino acid unit is in the L, or naturally occurring, form. The thio members of the $\beta$-mercaptopropionic acid (1) and cysteine (6) units are added for clarity in certain structural formulas.

Exemplary of the peptide art designations used herein are the following: dPen, $\beta$-mercapto-$\beta$,$\beta$-dimethylpropionic acid; Mpr, $\beta$-mercaptopropionic acid; Mpr(Et), $\beta$-mercapto-$\beta$,$\beta$-diethylpropionic acid; Pmp, $\beta$-mercapto-$\beta$,$\beta$-cyclopentamethylenepropionic acid; Gly, glycine; Tyr, tyrosine; Tyr(Et), ethyl ether of tyrosine; D-Tyr(Et), O-ethyl-D-tyrosine; L-Tyr(Et), O-ethyl-L-tyrosine; Arg, arginine; MeArg, N-methylarginine; HArg, homoarginine; Phe, phenylalanine; Cad, cadaverine, $NH_2(CH_2)_5NH_2$; Val, valine; Lys, lysine; Orn, Ornithine; Cha, cyclohexyl-alanine; Ile, isoleucine; Gln, glutamic acid amide or glutamine; Lysine, lysine; Nle, norleucine; Leu, leucine; Ala, alanine; Abu, $\alpha$-amino-n-butyric acid; O-AlkTyr, O-alkyltyrosine; 4'-AlkPhe; 4'-alkylphenyl-alanine; Chg, cyclohexylglycine; Clz, 2 chlorobenzyloxy carbonyl; VSP, vasopressin; AVP, 8-arginine vasopressin; VAVP, 4-valine-8-arginine vasopressin; Asn, asparagine; Tos, tosylate; BHA, benzhydrylamine; DIEA, diisopropylethylamine; 4-MeBzl, 4-methylbenzyl; TFA, trifluoroacetic acid; DCC, dicyclohexylcarbodiimide; HOBT, 1-hydroxybenzotriazole; ACM, acetamidomethyl.

DESCRIPTION OF THE INVENTION

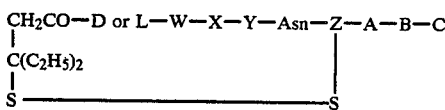

in which:

A is a single bond or a D or L-isomer of Pro, MeArg, HArg or Arg;

B is a D or L-isomer of MeArg, HArg, Arg, Lys, Orn or $NR_1(CH_2)nNR_2R_3$; and

C is Gly, Gly($NH_2$), OH or $NH_2$, or when B is $NR_1(CH_2)nNR_2R_3$, C is absent;

$R_1$ and $R_2$ are each H or $CH_3$; $R_3$ is H or C($=$NH)$NH_2$;

W is Phe, 4'-Alk Phe, Ile, Cha, Tyr or O-Alk Tyr;

X is Phe, 4'-Alk Phe, O-Alk Tyr, Ile or Tyr;

Y is Val, Ile, Abu, Chg, Gln, Lys, Cha, Nle, Leu, Ala or Gly;

Z is D or L isomer of Cys; and n is 2 to 6; or a pharmaceutically acceptable salt or ester prodrug thereof.

A subgeneric group of the compounds of formula I are those in which the Tyr(Et) is the D-isomer; A is Pro or Arg; B is Arg; and C is Gly($NH_2$) or $NH_2$.

"Alk" represents a lower alkyl of 1 to 4 carbons.

Also included in this invention are various derivatives of the compounds of formula I such as addition salts, prodrugs in ester form and complexes. The addition salts may be either salts with pharmaceutically acceptable cations such as $NH^{\oplus}$, $Ca^{\oplus\oplus}$, $K^{\oplus}$ or $Na^{\oplus}$ at a terminal acid group, when present, or with a pharmaceutically acceptable salt at a basic center of the peptide (as in Cad or Arg unit). The acetate salt forms are especially useful although hydrochloride, hydrobromide and salts with other strong acids are useful. In the isolation procedures outlined in the Examples, the peptide product is often isolated as the acetate salt. The compounds also form inner salts or zwitter ions as when a free terminal carboxy group is present.

Prodrugs are derivatives of the compounds of formula I which degrade to the parent compound in vivo. The ester prodrug forms are, for example, lower alkyl esters of the acids of formula I which have from 1-8 carbons in the alkyl radical or aralkyl esters which have 6-12 carbons in the aralkyl radical such as various benzyl esters. Such ester derivatives are prepared by methods known to the art. Other latentiated derivatives of the compounds of formula I will be obvious to those skilled in the art. "Complexes" include various solvates, such as hydrates or alcoholates, or those with supporting resins, such as a Merrifield resin.

The compounds of formula I are prepared by cyclizing a linear peptide intermediate of this invention by means of the two mercapto groups located, respectively, in the cysteine unit at position 6 and in the $\beta$-mercaptopropionic acid unit at position 1. The cyclization reaction occurs in the presence of a mild oxidizing agent which, at high dilution, is capable of oxidizing intramolecularly the dimercaptan to a disulfide.

Oxidation of the following linear peptide;

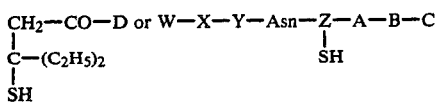

II in which A, B, C, W, X, Y and Z are as defined for formula I, is carried out as described generally above. For example, an excess of an alkali metal ferricyanide, such as potassium or sodium ferricyanide, is used. The linear intermediate is dissolved in a suitable unreactive solvent, preferably in an aqueous solvent, at a neutral pH, about 7–7.5. The reaction is run at ambient temperature, or lower, until substantially complete. Lower alcohols, such as methanol, may be added. Preferably, the concentrations of the linear peptide dimercaptan and the oxidizing agent are low, say 0.01 molar concentration of oxidizing agent in several liters of aqueous solution to cyclize 1–6 grams of dimercaptan.

Other mild oxidation agents having an oxidation potential roughly equivalent to ferricyanide may also be used for the ring closure reaction. Oxygen, iodine, diiodoethane, hydrogen peroxide or cupric catalyzed oxidation are alternatives. Of course, one skilled in the art will recognize that certain cyclization methods are not appropriate if an interfering reaction site is present in the structure of the starting material of formula II. The linear mercaptan starting material may or may not have protecting groups common in the art present at the various amino acid units or at the mercapto positions. In the former case, the protecting groups are removed after cyclization. In the case of the ACM-SH protecting groups, removal of the protective group and cyclization may both be accomplished using iodine in aqueous methanol. Usually, however, the free linear peptide is cyclized.

The peptides of formula I are conveniently isolated by acidifying the aqueous oxidation mixture, such as using glacial acetic acid, and passing the reaction mixture over an ion-exchange chromatographic column, for example, over a weakly acid, acrylic resin column with elution using buffered base, or by gel filtration over a bead-formed gel prepared by cross-linking dextran with epichlorohydrin. Often, the acetate salt is isolated by this method.

The important intermediates of formula II, in free or protected form are conveniently prepared using solid-phase methods of peptide synthesis as discussed in M. Manning et al., J. Med. Chem. 25 46 (1982). A commercial benzhydrylamine support resin (BHR) is used to prepare the amide end products of formula I, i.e. in which C is $NH_2$ or $Gly(NH_2)$, (the amides), and a chloro-methyl support resin (CMR) is used to prepare the acid compounds of formula I, i.e. in which C is OH or Gly, (the acids). Solution or enzymatic synthetic methods can also be used.

The peptide chain of the linear peptides of formula II is built up, stepwise, proceeding from the C-terminal unit working toward the characterizing unit 1. Each unit is properly protected as known in the peptide art and as described below. The sequence of step reactions is conveniently carried out in a Beckman 990-B peptide synthesizer without isolation of each intermediate peptide. The details of the overall synthetic procedure are in the working examples presented hereinafter.

The various amino acids, which are consecutively added to the resin supported chain are protected as known to the art. For example, the Boc protecting group is used for an amino group especially at the α-position of the amino acid; ethylcarbamoyl, adamantyl, t-butyl, acetamidomethyl, trityl or an optionally substituted benzyl, for the mercapto groups at the propionic acid and Cys units; nitro; carbobenzoxy, methylene-2-sulfonyl or tosyl for a Arg, MeArg or HArg unit; and ethyloxycarbonyl or an optionally substituted carbobenzoxy (Z) for amino or hydroxyl groups. The protective groups should, most conveniently, be those which are easily removed, such as using acid treatment for the tert.-butyloxycarbonyl (Boc) group, sodium-liquid ammonia or modified catalytic hydrogenation for the benzyl or carbobenzoxy groups.

The protected linear peptide intermediate is split from the carrying resin matrix, for example, by using ammonia in an aqueous miscible solvent, and, then, is treated to remove the protective groups, such as by using sodium-liquid ammonia. This procedure gives the amide derivative of the linear peptide intermediate.

More conveniently, the two steps are combined by treating the resin supported peptide with anhydrous hydrogen fluoride using a suitable carbonium ion scavenger, such as anisole, to give the linear peptide intermediate of formula II in good yield.

An alternative procedure for preparing the compounds of formula I is the attachment of one or more of the side chain units (A, B or C) to the acid form of the next lower cyclized peptide. For example, compounds of formula I in which B is cadaverine are prepared by the method described in U.S. Pat. No. 4,543,349. The condensation comprises the condensation of the polypeptide in the carboxy terminal acid form with the side chain unit whose acid or second basic center is protected, usually in the presence of DCC with HOBT or DMAP.

The compounds of this invention have potent $V_2$ vasopressin antagonist activity. Vasopressin is known to contribute to the anti-diuretic mechanism of action within the kidney. When the action of the compounds of this invention antagonizes that of the natural anti-diuretic hormone (ADH), the body excretes water due to an increased permeability of the terminal portions of the renal tubule. This mechanism of action is at the vasopressin receptors ($V_2$-receptors) located on the plasma membrane of certain renal epithelial cells. It is antagonistic in nature, not agonistic.

Any patient suffering from the syndrome of inappropriate antidiuretic hormone secretion (SIADH) or from an undesirable edematous condition is a target for compounds which have substantial $V_2$-antagonist activity. Examples of clinical conditions indicated for such compounds include hypertension, hepatic cirrhosis, congestive heart failure or a component of any traumatic condition resulting from serious injury or disease.

The compounds of the present invention are, therefore, potent antagonists at $V_2$-receptor sites as well as lower activity at the $V_1$-receptor sites and have a potent aquaretic or water diuretic activity in human or animal patients in need of such activity.

The compounds of this invention, therefore, are used to induce water diuresis via a $V_2$-antagonism as noted above in patients in need of such antagonist treatment by administration internally, particularly parenterally or by insufflation, to said patients. A non-toxic but effective quantity of the chosen compound is preferably combined with a pharmaceutical carrier. Dosage units contain a nontoxic, effective quantity of the active ingredient selected from the range 0.05-50 mcg/kg, preferably 1-15 mcg/kg, based on a 70 kg patient. The dosage units are administered from 1 to 5 times daily or by continuous intravenous drip.

The pharmaceutical compositions of this invention, which contain an active ingredient of formula I, comprise a dosage unit quantity as described above dissolved or suspended in a standard liquid carrier. Such a carrier is isotonic saline. The composition is often used in an ampoule or a multiple dose vial suitable for parenteral injection, such as for intravenous, subcutaneous or intramuscular administration. A composition for insufflation may be similar but is often administered in a metered dose applicator or inhaler. Pulverized powder compositions may be used along with oily preparations, gels, buffers for isotonic preparations, emulsions or aerosols.

Antagonistic activity at the $V_2$-vasopressin receptors is determined in a protocol which determines in vivo diuretic activity in the hydropenic rat ($ED_{300}$ μg/kg). This procedure is described in the literature: F. Stassen et al., 1st International Conference on Diuretics, Miami, FL., March (1984).

Compound A: [1-(β,β-diethyl-β-mercaptopropionic acid)-2-(O-ethyl-D-tyrosine)-4-valine-8-arginine]-vasopressin; $ED_{300}$, 27.0 μg/kg.

Compound B: [1-(β,β-diethyl β-mercaptopropionic acid)-2-(O-ethyl-D-tyrosine)-4-valine-8-arginine-9-desglycine]-vasopressin; $ED_{300}$, 11.9 (3) μg/kg.

Compound C: [1-(β,β-diethyl-β-mercaptopropionic acid)-2-(O-ethyl-L-tyrosine)-4-valine-8-arginine]-vasopressin, $ED_{300}$, 120.5 82 g/kg.

Compound D: [1-(β,β-dimethyl-β-mercaptopropionic acid)-2-(O-ethyl-D-tyrosine)-4-valine-8-arginine]-vasopressin; $ED_{300}$; 4950 μg/kg.

These data demonstrate the compounds of this invention, especially Compounds A and B, are very potent $V_2$-antagonists compared with a representative dPen[1] congener (Compound D). As such they represent the first potent $V_2$-antagonists whose structures do not have a cycloalkyl moiety at position 1.

The following examples are designed solely to teach the operation of this invention. All temperatures are degrees Centigrade. Nomenclature is standard in the peptide art.

EXAMPLE 1

Preparation of S-Protected
β,β-Diethyl-β-mercaptopropionic acid Intermediates (A). A 500 ml 3-neck round bottom flask equipped with a thermometer, an addition funnel, a mechanical stirrer and argon gas inlet and outlet was dried by a heating gun as the flask is purged with argon gas. 160 ml of toluene (molecular sieves dried) was, then, added followed by the addition of 9.48 g of a 60% dispersion of sodium hydride in mineral oil. This mixture was stirred for 15 minutes at which time 56.8 g of triethylphosphonoacetate was added dropwise over a 40 minute period. The temperature was maintained at 30° and cooling is employed when necessary. The resulted solution was stirred for 35 minutes at room temperature. To this solution, 20 g of 3-pentanone was, then, added dropwise. After complete addition, the reaction mixture was heated at 60° for 10-15 minutes. Cold water was, then, added. The two phases were separated. The aqueous layer was thoroughly extracted with ether. The organics were combined, washed with brine and dried over anhydrous sodium sulfate. The drying agent was removed by filtration and the filtrate was stripped on the rotavap. The residue was purified by silica gel chromatography eluted with hexane/ethyl acetate, 9:1 β,β-Diethylacrylic acid, ethyl ester, 13.8 g, was obtained.

7.3 Grams of the β,β-diethylacrylic acid, ethyl ester, and 5.5 ml (0.047 m) of benzylmercaptan together With 10 ml of piperidine in a 100 ml round bottom flask were heated at reflux overnight. Tlc. showed a new spot with a Rf value just slightly lower than that of the starting acrylic ester. The reaction mixture was diluted with 100 ml of ethyl acetate and then acidified with 1 N hydrochloric acid. The organic phase was separated, washed with brine and, then, stripped on the rotavap. The residue was hydrolyzed with 15 g of potassium carbonate in a mixture of 50 ml of methanol and 50 ml of water at reflux for 24 hours. The reaction mixture was concentrated under reduced pressure. The residue was diluted with water, extracted with 2×30 ml of ether. The aqueous was, then, acidified with phosphoric acid to pH=2. It was thoroughly extracted with ether. The extracts were combined, washed with brine and dried over anhydrous magnesium sulfate. Removal of drying agent and solvent gave 2.2 g of S-benzylmercapto product which was recrystallized from hexane; mp 75.0°-75.5°. Nmr and ir spectral data are consistent with the β,β-diethyl-β-(S-benzylmercapto)-propionic acid.

(B). A mixture of 5.1 g of the acrylic ester from A and 5 ml of p-methylbenzylmercaptan in 8 ml of piperidine in 25 ml round bottom flask was heated at reflux overnight. The reaction mixture was diluted with ice-water (50 ml) and ethyl acetate (30 ml). The resulted solution was acidified with conc. hydrochloric acid to pH=2. The organic layer was separated, washed with cold 1N alkali solution, brine and dried over anhydrous sodium sulfate. Removal of the drying agent and solvent gave 5.2 g of β,β-diethyl-β-(S-p-methylbenzyl)propionic acid, ethyl ester. This ester was, then, hydrolyzed with 12.5 g of potassium carbonate in a mixture of 35 ml of water, 35 ml of methanol and 70 ml of tetrahydrofuran at refluxing temperature for 24 hours.

The solution was stripped in a rotavap, diluted with 100 ml of water. This aqueous solution was extracted twice with 50:50 ether/hexane, and was, then, acidified with conc. hydrochloric acid. The mixture was extracted thoroughly with ether. The ether extracts were combined, washed with brine and dried. Removal of the drying agent and solvent gave 3.2 g of oily residue which is then crystallized from hexane. Nmr and ir spectral data are consistent with desired β,β-diethyl-β-(S-p-methyl-benzyl)-propionic acid.

(C). The protected β,β- diethyl-β-mercaptopropionic acids were also prepared conveniently by refluxing a mixture of β,β-diethyl-acrylic acid, the selected mercaptan and piperidine for 18-24 hours, then isolating the product by treatment with acid.

EXAMPLE 2

Boc-D-Tyr(Et)-Phe-Val-Asn-Cys(S-Bzl)-Pro-Arg-(Tos)-Gly-OCH$_2$C$_6$H$_5$-resin 5.1 Grams (3 mmoles) of Boc-Val-Asn-Cys(S-Bzl)-Pro-Arg(Tos)-Gly-OCH$_2$φ-resin was further coupled sequentially with Boc-Phe and Boc-D-Tyr(Et) using 9 mmoles of amino acid and 9 mmoles of DCC (1.85 g)

and 18 mmoles of 1-hydroxybenzotriazole (2.43 g) as catalyst. 2.38 Grams of BocPhe and 2.7 g. of Boc-D-Tyr(Et) were used. The final peptide resin was washed with methylene chloride and vacuum dried to give 5.5 g (3 mm) of titled product.

EXAMPLE 3

Mpr(Et)—D-Tyr(Et)—Phe—Val—Asn—Cys—
                                       |
                                       —Pro—Arg—GlyNH$_2$ 1.55 Grams (0.83 mmole) of Boc-D-Tyr(Et)-Phe-Val-Asn-Cys(S-Bzl)-Pro-Arg(Tos)-Gly-OCH$_2\phi$-resin from Example 2 was coupled with 150 mg of $\beta$-(S-benzyl-mercapto)-$\beta,\beta$-diethylpropionic acid from Example 1A with 300 mg of dimethylaminopyridine (DMAP) using DCC as coupling reagent by means of a Beckman Peptide Synthesizer Model #990B. A second coupling using one half of the materials was carried out to ensure complete reaction. 1.75 Grams of protected peptide resin was obtained.

This protected peptide resin was subjected to ammonolysis using saturated ammonia/methanol (350 ml) at room temperature for 3 days. After evaporated to dryness under reduced pressure, the residue was thoroughly extracted with dried dimethylformamide (50 ml). The combined extracts were concentrated to 10 ml which was, then, precipitated with ether. The precipitate was collected by filtration, washed with ether and dried in vacuo.

This crude protected peptide (1.21 g) was dissolved in liquid ammonia (60 ml) and treated with sodium/liquid ammonia solution for deprotection of all the side chains and splitting the resin off. It was, then, oxidized in 4 liter of aqueous solution at pH=7.2-7.4 using 0.01M aqueous potassium ferricyanide solution. After complete oxidation, the pH of the aqueous solution was adjusted to pH 4.5 by addition of glacial acetic acid. The solution was passed through a weakly acidic ion exchange (Bio-Rex 70) column (11×2.5 cm) slowly. The column was eluted with water and then with aqueous pyridine/acetic acid buffer solution. Concentration of the eluent and lyophilization from 0.2N acetic acid gave 580 mg of the crude titled product.

The crude pruduct was purified by counter-current distribution using BAW system (n-BuOH/HOAc/H$_2$O, 4:1:5) with 240 transfers. Two samples were obtained, with 223.9 mg as the major sample and 52.8 g as the minor sample.

60 Mg of the major sample was further purified by preparative HPLC with a C$_{18}$ column using 40% acetonitrile in water with 0.1% trifluoroacetic acid as mobile phase. 28 Mg of pure titled product was obtained.

Satisfactory FAB-MS for its molecular weight and fragments and amino acid analysis were obtained: HPLC-1 peak; Tlc-1 spot; peptide content, 66%. Amino acid analysis: Asp (1.09), Pro (1.4), Gly (0.97), Cys (0.76), Val (1.07), Tyr (1.01), Phe (1.02), Arg (1.00).

EXAMPLE 4

Mpr(Et)(S-4-MeBzl)-D-Tyr(Et)-Phe-Val-Asn-Cys(S-4-MeBzl)-Arg(Tos)-BHA-resin 1.8 Grams (2.3 mmoles) of commercial BHA-resin was coupled with the appropriately protected amino acid sequentially by means of Beckman Peptide Synthesizer model #990B using DCC as coupling reagent, HOBT as catalyst and dimethylformamide/methylene chloride, 1:1, as solvent. In each coupling cycle, 6.6 mmoles of amino acid, 6.6 mmoles of DCC and 13.2 mmole of HOBT were used. 50% Trifluoroacetic acid in methylene chloride was used for deprotection of the Boc group. The mixture was neutralized with 7% diisopropylethylamine in methylene chloride. Completion of each coupling was monitored by the ninhydrin test. The final protected peptide resin was washed with a series of solvents (methylene chloride/ethanol.methylene chloride/methylene chloride) and, then, dried in vacuo. 3.4 Grams of the Boc-Phe-Val-Asn-Cys(4-MeBzl)-Pro-Arg(Tos)-BHA peptide-resin was obtained.

2.26 Grams of the Boc-Phe-Val-Asn-Cys(4-MeBzl)-Pro-Arg(Tos)BHA resin was further coupled with 1.13 g (3.4 mmoles) of Boc-D-Tyr(Et) as described above to give Boc-D-Tyr(Et)-Phe-Val-Asn-Cys(4-MeBzl)-Pro-Arg(Tos)BHA resin. One half of this peptide resin was, then, coupled with 400 mg (1.5 mmoles) of $\beta$-(S-4-MeBzl)-$\beta,\beta$-diethylpropionic acid on a manual solid phase shaken using 309 mg of DCC and 183 mg of dimethylaminopyridine in methylene dichloride in the usual coupling cycle. A second coupling to ensure reaction was carried out by using 200 mg of Mpr(Et)-(S-MeBzl)-OH and 1.55 mg of DCC and 92 mg of DMAP. Negative ninhydrin test was obtained. This protected peptide resin was, then, dried in vacuo overnight at room temperature.

EXAMPLE 5

Mpr(Et)—D-Tyr(Et)—Phe—Val—Asn—Cys—Pro—ArgNH$_2$
         |_____|

The one-half mmole of protected peptide resin intermediate from Example 4 was cleaved and deprotected with anhydrous liquid hydrogen fluoride (25 ml) and 1 ml of anisole at 0° for 1 hour. The HF was evaporated in vacuo. The residue was treated with anhydrous ether to remove the anisole and other by.products. The peptide was extracted from the resin with 2×6 ml of dimethylformamide and 3×10 ml of 50% aqueous acetic acid. The combined extracts were diluted to 2.2 l with water. The resulting solution was adjusted to pH 7.2 with ammonium hydroxide and was treated with 0.01M of potassium ferricyanide dropwise until a pale yellow color persisted for 15 minutes. The pH was adjusted to 4.5 by addition of acetic acid. This solution was passed through a weakly acidic ion exchange resin (Bio-Rex 70, 50-100 mesh, 11×2.5 cm column) very slowly. The column was eluted with water and, then, with aqueous pyridine/acetic acid buffer (pyridine/acetic acid/water 30:4:66). The pyridine buffer eluent was collected and evaporated under reduced pressure. The residue was taken up in 0.2N of acetic acid, then lyophilized to give 119 mg of crude titled product.

The crude product was purified by counter current distribution using n-butanol/acetic acid/water, 4:1:5 with a two phase system using 240 transfers.

Based on Tlc results, they were pooled into 2 samples: I, 49.5 mg; II, 32 mg. HPLC showed II with a trace of impurities.

Analytical data of sample I: HPLC, single peak; Tlc, single spot; FAB-MS, satisfactory molecular ions and fragments (mol. wt. 1066). Peptide content; 79.6%. Amino acid analysis; Asp (1.00), Pro (1.19), Cys (0.42), Val (0.93), Tyr (0.95), Phe (1.00), Arg (0.98).

EXAMPLE 6

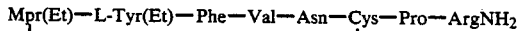
Mpr(Et)—L-Tyr(Et)—Phe—Val—Asn—Cys—Pro—ArgNH₂

0.5 Mmoles of Boc-Phe-Val-Asn-Cys(4Me-Bzl)-Pro-Arg(Tos)BHA resin, obtained as described in Example 4, was further coupled with Boc-L-Tyr(Et) and Mpr(Et)(S-MeBzl)-OH in a manually operated synthesizer using DCC as coupling reagent.

The protected peptide resin was cleaved and deprotected with anhydrous liquid HF (25 ml) with 2 ml of anisole at 0° for 1 hour. The HF was evaporated and residue was washed with anhydrous ether to remove the anisole and ether. The peptide was extracted from the residue with dimethylformamide and 50% aqueous acetic acid. The combined extracts were cyclized in a diluted aqueous solution (2 l) at pH=7.2 with 0.01M potassium ferricyanide solution. The pH of the resulted solution was adjusted to 4.5 with glacial acetic acid. The solution was passed through a weak ion exchange column (Bio-Rex 70, 2.5×11 cm, at a rate of 100 ml/hr). The column was washed with water and eluted with pyridine/acetic acid/water buffer (30:4:66; v/v). The collected basic eluent (120 ml) was evaporated under reduced pressure. The residue was taken up in 0.2N acetic acid, then lyophilized to give the crude titled product.

The peptide was purified by partition chromatography over Sephadex G-15 using a B/A/W, 4:1:5 system, 80 tubes were collected. Based on the tlc results, the fractions containing the desired product were pooled into three fractions of various purity:

| A = 14.6 mg | HPLC pure |
| B = 12.6 mg | trace of impurity |
| C = 26.8 mg | trace of impurity |

B and C were combined, further purified by preparative HPLC on a C₁₈ column to give 24.0 mg product. The product obtained was submitted for amino acid analysis and fast atom bombardment-mass spectrum. Analytical results: HPLC, single peak; Tlc, 1 spot; FAB-MS, satisfactory molecular ions and dragments (mol. wt. 1066); Peptide content; 55.5%. Amino acid analysis; Asp, (1.00), Pro (0.66), Cys (0.55), Val (1.06), Tyr (0.57), Phe (1.01), Arg (1.10).

EXAMPLE 7

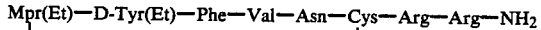
Mpr(Et)—D-Tyr(Et)—Phe—Val—Asn—Cys—Arg—Arg—NH₂

The protected peptide intermediate resin, Mpr(Et)(S-4-MeBzl)-D-Tyr(Et)-Phe-Val-Asn-Cys(4-MeBzl)-Arg(Tos)-Arg(Tos)-BHA is synthesized by solid-phase methods on benzhydrylamine resin (BHA). On a shaker, 1.0 mmol of the BHA-resin is used. All amino acids are protected as tert.-butyloxycarbonyl (Boc) on the α-amine and, then, coupled sequentially using DCC/HBT. The Mpr (Et)-(S-4-MeBzl)is coupled using DCC/DMAP. The peptide is cleaved from the resin with deprotection of the side-chain protecting groups by using anhydrous HF (30 ml) in presence of anisole (3.0 ml) at 0° for 60 minutes. After evaporation in vacuo to dryness, the residue is washed with anhydrous ether. The crude peptide is extracted with dimethylformamide (50 ml) and 40% acetic acid (50 ml) into 3.5 liters of water previously adjusted to pH 4.5. The aqueous-diluted disulfhydryl octapeptide mixture is oxidatively cyclized with 0.01M potassium ferricyanide at pH 7.2 until a pale yellowish solution persists for 15 minutes. The pH of the solution is adjusted to 4.5 using glacial acetic acid. It is passed through a weakly acid, acrylic resin (Bio-Rex 70) column. The column is eluted with pyridine-acetate buffer (30:4:66, pyridine/glacial acetic acid/water/vv). The pyridine acetate is removed by distillation in vacuo. The residue is lyophilized from dilute acetic acid to give the partially purified titled peptide. Purification is as described above.

EXAMPLE 8

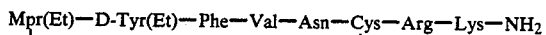
Mpr(Et)—D-Tyr(Et)—Phe—Val—Asn—Cys—Arg—Lys—NH₂

The protected peptide intermediate resin, Mpr(Et)(S-4-MeBzl)-D-Tyr(Et)-Phe-Val-Asn-Cys(4-MeBzl)-Arg(Tos)-Lys(ClZ)-BHA is synthesized by solid-phase methods on benzhydrylamine resin (BHA). On a shaker, 1.0 mmol of the BHA resin is used. All amino acids are protected as tert.-butyloxycarbonyl (Boc) on the α-amine and, then, coupled sequentially using DCC/HBT. The Mpr(Et)-(S-4-MeBzl)is coupled using DCC/DMAP. The peptide is cleaved from the resin with deprotection of the side-chain protecting groups by using anhydrous HF (30 ml) in presence of anisole (3.0 ml) at 0° for 60 minutes. After evaporation in vacuo to dryness, the residue is washed with anhydrous ether. The crude peptide is extracted with dimethylformamide (50 ml) and 40% acetic acid (50 ml) into 3.5 liters of water previously adjusted to pH 4.5. The aqueous-diluted disulfhydryl octapeptide mixture is oxidatively cyclized with 0.01M potassium ferricyanide at pH 7.2 until a pale yellowish solution persists for 15 minutes. The pH of the solution is adjusted to 4.5 using glacial acetic acid. It is passed through a weakly acid, acrylic resin (Bio.Rex 70) column. The column is eluted with pyridine-acetate buffer (30:4:66, pyridine/glacial acetic acid/water/vv). The pyridine acetate is removed by distillation in vacuo. The residue is lyophilized from dilute acetic acid to give the partially purified titled peptide. Purification is as described above.

EXAMPLE 9

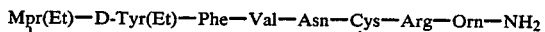
Mpr(Et)—D-Tyr(Et)—Phe—Val—Asn—Cys—Arg—Orn—NH₂

The protected peptide intermediate resin, Mpr(Et)(S-4-MeBzl)-D-Tyr(Et)-Phe-Val-Asn-Cys(4-MeBzl)-Arg(Tos)-Arg(ClZ)-BHA is synthesized by solid-phase methods on benzhydrylamine resin (BHA). On a shaker, 1.0 mmol of the BHA-resin is used. All amino acids are protected as tert.-butyloxycarbonyl (Boc) on the α-amine and, then, coupled sequentially using DCC/HBT. The Mpr(Et)-(S-4 MeBzl)is coupled using DCC/DMAP. The peptide is cleaved from the resin with deprotection of the side-chain protecting groups by using anhydrous HF (30 ml) in presence of anisole (3.0 ml) at 0° for 60 minutes. After evaporation in vacuo to dryness, the residue is washed with anhydrous ether. The crude peptide is extracted with dimethylformamide (50 ml) and 40% acetic acid (50 ml) into 3.5 liters of water previously adjusted to pH 4.5. The aqueous-diluted disulfhydryl octapeptide mixture is oxidatively cyclized with 0.01M potassium ferricyanide at pH 7.2 until a pale yellowish solution persists for 15 minutes. The pH of the solution is adjusted to 4.5 using glacial acetic acid. It is passed through a weakly acid, acrylic resin (Bio-Rex 70) column. The column is eluted with pyridine-acetate buffer (30:4:66, pyridine/glacial acetic acid/water/vv). The pyridine acetate is removed by distillation in vacuo. The residue is lyophilized from dilute acetic acid to give the partially purified titled peptide. Purification is as described above.

EXAMPLE 10

Mpr(Et)—D-Tyr(Et)—Phe—Val—Asn—Cys—Arg—Arg(OH):
|_____|

The protected peptide intermediate used, Mpr(Et)(S-4-MeBzl)-D-Tyr(Et)-Phe-Val-Asn-Cys(4-MeBzl)-Arg(Tos)-Arg(Ios)-OCH$_2$C$_6$H$_4$-Resin is synthesized on 1.0 mmol of Boc-Arg(Tos)-O-Bzl-Resin (purchased from Peninsula Laboratories). The HF cleavage and oxidation with 0.01M ferricyanide are performed as described above. The dilute solution is partially purified through a reversed phase C-18 column. The titled peptide is eluted with 50% aqueous acetonitrile containing 0.1% trifluoroacetic acid. Further purification by preparative HPLC as described above.

EXAMPLE 11

Mpr(Et)—D-Tyr(Et)—Phe—Val—Asn—Cys—Pro—Cad
|_____|

To a solution of the Mpr(Et)$^1$-proline heptapeptide, prepared as described in U.S. Pat. No. 4,543,349, (29.7 mg, 0.0331 mmol) and mono-Boc-1,5-diaminopentane (20.2 mg, 0.0996 mmol) in dimethylformamide (400 1), dicyclohexylcarbodiimide (10.3 mg, 0.05 mmol) and 1-hydroxybenzotriazole hydrate (13.4 mg, 0.1 mmol) are added. The reaction mixture is stirred at room temperature for 19 hours. The dimethylformamide is, then, removed under vacuum. The residue is treated with trifluoroacetic acid at 0° for 2 hours. After this time, the trifluoroacetic acid is removed under vacuum and the residue in 1% acetic acid is passed over a BioRex 70 (H+) ion exchange column. The basic products are washed off the ion exchange column with pyridine buffer (H$_2$O/pyridine/HOAc, 66:30:4) and evaporated. Final purification by prep HPLC (5$\mu$ Ultrasphere ODS) gives the title compound.

EXAMPLE 12

Using the methods of synthesis described in detail above, the following specific compounds are produced. Compounds d, f, g and h may further be prepared by guanidation of the corresponding lysine-containing peptide according to the method described in Ali et al., J. Med. Chem., 29, 984, 1986.
a. [1-($\beta,\beta$-diethyl-$\beta$-mercaptopropionic acid)-2-(O-ethyl-D-tyrosine)-4- valine-7-desproline 8-arginine]vasopressin;
b. [1-($\beta,\beta$-diethyl-$\beta$-mercaptopropionic acid)-2-(O-ethyl-D-tyrosine)-4-valine-7-desproline-8-arginine-9-desglycine]-vasopressin;
c. [1-($\beta,\beta$-diethyl-$\beta$-mercaptopropionic acid)-2-(O-ethyl-D-tyrosine)-4-valine-8-N-methylarginine]-vasopressin;
d. [1-($\beta,\beta$-dimethyl-$\beta$-mercaptopropionic acid)-2-(O-ethyl-D-tyrosine)-4-valine-8-homoarginine]vasopressin;
e. [1-($\beta,\beta$-diethyl-$\beta$-mercaptopropionic acid)-2-(O-ethyl-D-tyrosine)-4-valine-8-D-arginine]vasopressin;
f. [1-($\beta,\beta$-diethyl-$\beta$-mercaptopropionic acid)-2-(O-ethyl-D-tyrosine)-4-valine-7-desproline-8-arginie-9-homoarginine]vasopressin;
g. [1-($\beta,\beta$-diethyl-$\beta$-mercaptopropionic acid)-2-(O-ethyl-D-tyrosine)-4-valine-7-desproline-8,9-bishomoarginine]vasopressin;
h. [1-($\beta,\beta$-dimethyl-$\beta$-mercaptopropionic acid)-2-(O-ethyl-L-tyrosine)-4-valine-8,9-bisarginine]vasopressin.

EXAMPLE 13

Parenteral Dosage Unit Compositions

A preparation which contains 0.01 mg of the peptide of Example 3 as a sterile dry powder for parenteral injection is prepared as follows: 0.5 mg of peptide is dissolved in 1 ml of an aqueous solution of 20 mg of mannitol. The solution is filtered under sterile conditions into a 2 ml ampoule and lyophilized. The reconstituted solution is administered to a patient in need of vasopressin V$_2$-antagonist treatment as necessary, from 1–5 times daily by injection, or in an equivalent continuous i.v. drip injection.

Nasal Dosage Unit Compositions 2.5 Mg of a finely ground peptide of this invention, such as the product of Example 2, is suspended in a mixture of 75 mg of benzyl alcohol and 1.395 g of a suspending agent such as a commercial mixture of semi-synthetic glycerides of higher fatty acids. The suspension is placed in an aerosol 10 ml container which is closed with a metering valve and charged with aerosol propellants. The contents comprise 100 unit doses which are administered intranasally to a subject in need of aquaretic thereapy from 1–6 times a day.

What is claimed is:

1. A chemical compound having the formula:

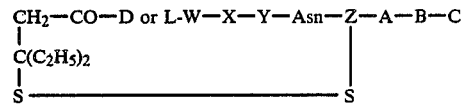

in which:

A is a single bond or a D or L-isomer of Pro, MeArg, HArg or Arg;

B is a D or L-isomer of MeArg, HArg, Arg, Lys, Orn or NR$_1$(CH$_2$)$_n$NR$_2$R$_3$;

C is Gly, Gly(NH$_2$), OH, NH$_2$, or when B is NR$_1$(CH$_2$)$_n$NR$_2$R$_3$, C is absent;

R$_1$ and R$_2$ are each H or CH$_3$;

R$_3$ is H or C(=NH)NH$_2$;

W is Phe, 4'-Alk Phe, Ile, Cha, Tyr or O-Alk Tyr; Tyr and O-Alk Tyr being D-isomers X is Phe, 4'-Alk Phe, O-Alk Tyr, Ile or Tyr;

Y is Val, Ile, Abu, Chg, Gln, Lys, Cha, Nle, Leu, Ala or Gly;

Z is D or L isomer of Cys;

n is 2 to 6; or a pharmaceutically acceptable salt or ester prodrug thereof; and "Alk" represents a lower alkyl of 1 to 4 carbons.

2. A compound of claim 1 in which A is Pro and C is NH$_2$.

3. A compound of claim 1 in which A is Pro and C is Gly(NH$_2$).

4. A compound of claim 1 in which A and B are both Arg.

5. A compound of claim 1 in which A is MeArg.

6. A compound of claim 1 in which the compound is [1-($\beta,\beta$-diethyl-$\beta$-mercaptopropionic acid)-2-(O-ethyl-D-tyrosine)-4-valine-8-arginine]vasopressin or a pharmaceutically acceptable salt thereof.

7. A compound of claim 1 in which the compound is [1-$\beta,\beta$-diethyl-$\beta$-mercaptopropionic acid)-2-(O-ethyl-D-tyrosine)-4-valine-8-arginine-9-desglycine]vasopressin or a pharmaceutically acceptable salt thereof.

8. A pharmaceutical composition having vasopressin V$_2$-antagonist activity comprising a pharmaceutical carrier and, dispersed therein, an effective therefor but nontoxic quantity of a compound of claim 1.

9. A pharmaceutical composition having vasopressin V$_2$-antagonist activity comprising a pharmaceutical carrier and, dispersed therein, an effective therefor but nontoxic quantity of the compound of claim 6.

10. A pharmaceutical composition having vasopressin V$_2$-antagonist activity comprising a phramaceutical carrier and, dispersed therein, an effective therefor but nontoxic quantity of the compound of claim 7.

11. The method of producing vasopressin V$_2$-antagonist activity in a patient in need thereof which comprises administering parenterally or intranasally to said patient an effective therefor, nontoxic quantity of a compound of claim 1.

12. The method of producing vasopressin V$_2$-antagonist activity in a patient in need thereof which comprises administering parenterally or intranasally to said patient an effective therefor, nontoxic quantity of the compound of claim 6.

13. The method of treating congestive heart failure in a patient in need thereof which comprises administering parenterally or intranasally to said patient an effective therefor, nontoxic quantity of a compound of claim 1.

14. The method of treating congestive heart failure in a patient in need thereof which comprises administering parenterally or intranasally to said patient an effective therefor, nontoxic quantity of the compound of claim 6.

15. The method of treating hypertension in a patient in need thereof which comprises administering parenterally or intranasally to said patient an effective therefor, nontoxic quantity of a compound of claim 1.

16. The method of treating hypertension in a patient in need thereof which comprises administering parenterally or intranasally to said patient an effective therefor, nontoxic quantity of the compound of claim 6.

* * * * *